United States Patent [19]

Murphy et al.

[11] Patent Number: 4,492,865
[45] Date of Patent: Jan. 8, 1985

[54] BOREHOLE INFLUX DETECTOR AND METHOD

[75] Inventors: Richard D. Murphy; Daniel F. Coope, both of Houston, Tex.

[73] Assignee: NL Industries, Inc., New York, N.Y.

[21] Appl. No.: 345,592

[22] Filed: Feb. 4, 1982

[51] Int. Cl.³ ............................................. G01V 5/12
[52] U.S. Cl. ...................................... 250/265; 250/254
[58] Field of Search ............... 250/265, 256, 254, 253, 250/268; 73/155; 175/48, 41, 40

[56] References Cited

U.S. PATENT DOCUMENTS

| | | | |
|---|---|---|---|
| 3,209,323 | 9/1965 | Grossman | 340/856 |
| 3,688,115 | 8/1972 | Antkiw | 250/269 |
| 4,034,218 | 7/1977 | Turcotte | 250/269 |
| 4,297,880 | 11/1981 | Berger | 73/155 |
| 4,392,377 | 7/1983 | Rankin | 73/155 |
| 4,412,130 | 10/1983 | Winters | 250/260 |

OTHER PUBLICATIONS

T. J. Hirst, M. Perlow, Jr., A. F. Richards, B. S. Burton, and W. J. Van Sciver, "Improved in situ Gamma-Ray Transmission Densitometer for Marine Sediments", *Ocean Engng.*, vol. 3, No. 1, (Jun. 1975), pp. 17–27.

*Primary Examiner*—Janice A. Howell
*Assistant Examiner*—Constantine Hannaher
*Attorney, Agent, or Firm*—Browning, Bushman, Zamecki & Anderson

[57] ABSTRACT

A system for detecting changes in drilling fluid density downhole during a drilling operation includes a radiation source and detector which are arranged in the outer wall of a drill string sub to measure the density of drilling fluids passing between the source and detector. Radiation counts detected downhole are transmitted to the surface by telemetry methods or recorded downhole, where such counts are analyzed to determine the occurrence of fluid influx into the drilling fluid from earth formations. Changes in the density of the mud downhole may indicate the influx of formation fluids into the borehole. Such changes in influx are determinative of formation parameters including surpressures which may lead to the encountering of gas kicks in the borehole. Gas kicks may potentially result in blowouts, which of course are to be avoided if possible. Hydrocarbon shows may also be indicative of producible formation fluids. The radiation source and detector in one embodiment of the system are arranged in the wall of the drill string sub to provide a direct in-line transmission of gamma rays through the drilling fluid.

31 Claims, 7 Drawing Figures

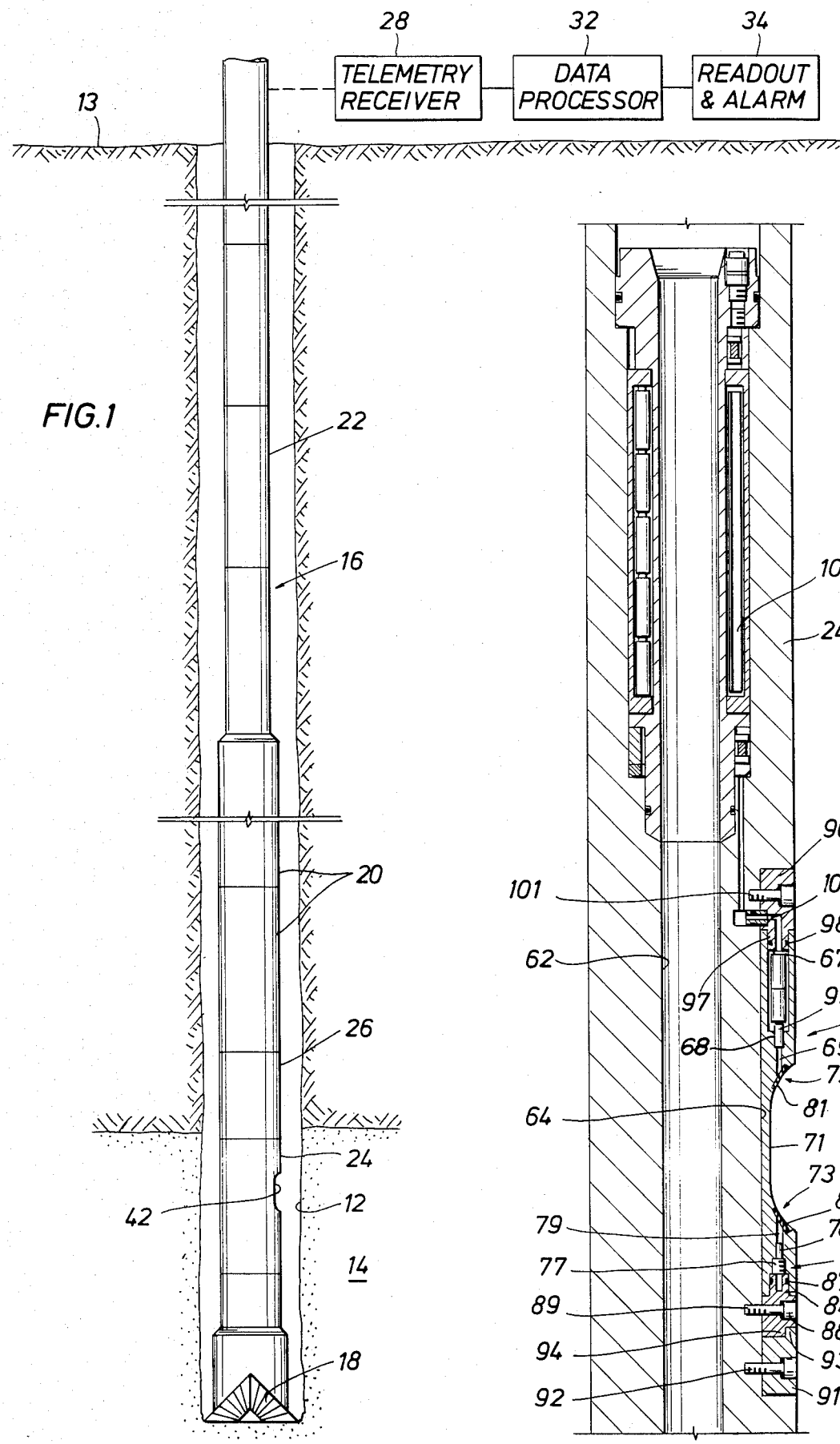

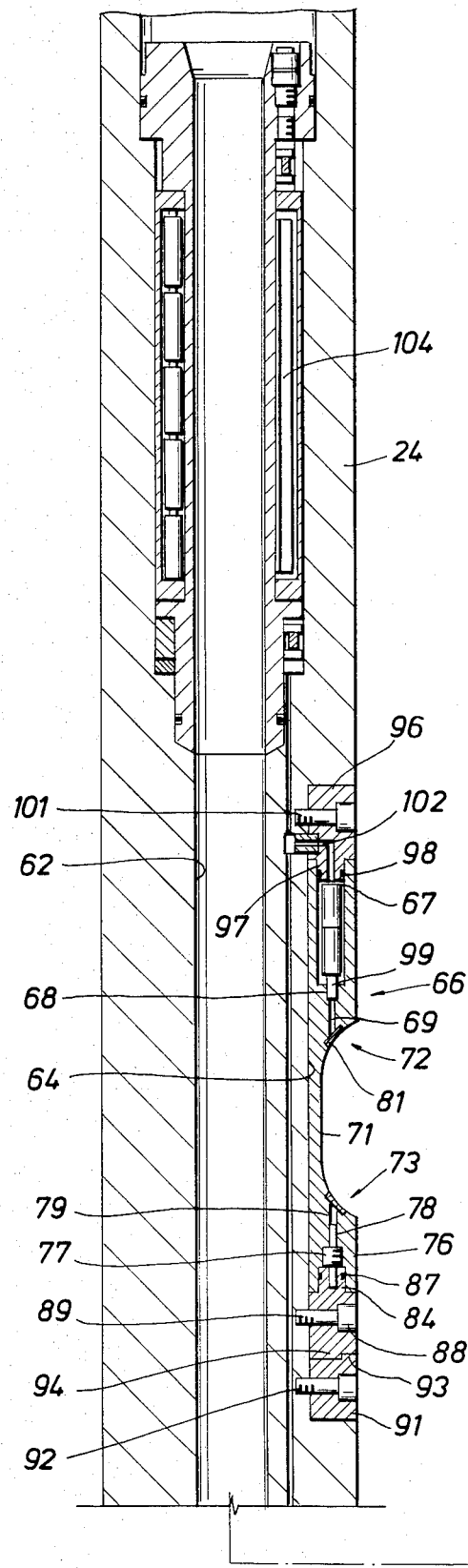
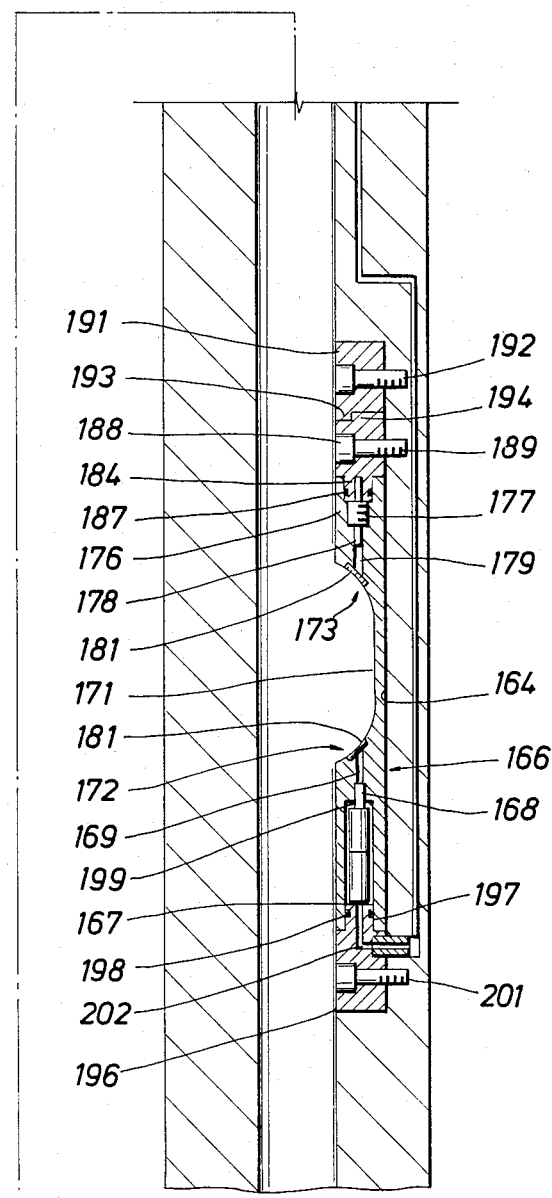
FIG.7

BOREHOLE INFLUX DETECTOR AND METHOD

BACKGROUND OF THE INVENTION

This invention pertains to a method and apparatus for logging borehole parameters during a drilling operation and more particularly to a borehole logging system for detecting downhole parameters relating to borehole fluid density.

Drilling fluid or "mud" as it is commonly called may vary in density or "mud weight" for a number of reasons. Such variations can result from changes in the quantity and density of cuttings (particles of formation); changes in the "mud program" at the surface, changes in temperature, etc. Variations in mud density also occur when gas or liquid enter the borehole from the formation. Such influx of formation fluids may likely be the result of formation surpressures or abnormally high pressures. For many reasons, the detection of such abnormal pressures is desirable. An in-depth discussion of this topic is found in a book entitled *Abnormal Formation Pressures* by Fertl, 1976, Elsevier Scientific Publishing Co. In any event, the detection and quantitative evaluation of overpressured formations is critical to exploration, drilling, and production operations for hydrocarbon resources. World-wide experience indicates a significant correlation between the presence and magnitude of formation pressures, and the shale/sand ratio of sedimentary sections of earth formations. Distribution of oil and gas is related to regional and local subsurface pressure and temperature environments. Knowledge of expected pore pressure and fracture gradients is the basis for efficiently drilling wells with correct mud weights, proper completions and killing of a well without excessive formation damage. Pressure detection concepts are especially important in balanced pressure drilling. Not only does the drilling rate decrease with a high overbalance of mud pressure versus formation pressure, but also lost circulation and differential pressure sticking of the drill pipe can readily occur. On the other hand an underbalance of mud pressure versus formation pressure can cause a pressure "kick." A well may kick without forewarning. Balanced drilling techniques often require only a fine margin between effective pressure control and a threatened blowout.

Present techniques for predicting or detecting abnormal formation pressure include drilling parameters such as drilling rate, torque and drag; drilling mud parameters such as mud gas cuttings, flow line mud weight, pressure kicks, flow line temperature, pit level and pit volume, mud flow rate; shale cutting parameters such as bulk density, shale factor, volume and size of cuttings; well logging data such as conductivity and resistivity surveys, downhole gravity data, nuclear magnetic resonance, and acoustic logs; and direct pressure measuring devices such as pressure bombs, drill-stem test data, and wire-line formation tests. Some comments on the above detection and prediction techniques are as follows: In monitoring flow line mud weight, frequent checks for weight reduction is an indicator for gas cutting and possible overpressures. Continuous mud weight recorders are commercially available to detect and record mud weight at the surface. Several drilling performance indicators can be deduced if mud density and flow rate in and out of the well and stand pipe pressure are accurately known. Formation pressure and salinity are associated and therefore equipment has been developed to measure the gain or loss of chlorides between inlet and flow lines in the mud stream to relate variations in drilling and pressure conditions. Also many modern drilling rig data units record inlet and flow-line mud resistivity. Variations in the total mud volume can be monitored by pit level indicators. Such devices register any large mud-volume reduction, as caused by lost circulation, and monitor large amounts of fluid entry into the borehole, e.g. from unexpected high formation pressures. A first indication of a kick while going into the hole is the observation that the pit level increases in excess of the mud displacement by the pipe run into the hole. Any abnormal rise in pit level caused by mud flow from the annulus will also be reflected in an increasing flow rate, which can be measured by a standard flowmeter. The investigation of shale cuttings is determinative of entry into overpressured environments. An increase in penetration rate, e.g. will result in increased volume of cuttings over the shale shaker. In transition zones, the shape of cuttings is angular and sharp rather than rounded as in normal pressure environments. Of the logging techniques available, the acoustic or sonic log is probably the best log for quantitative pressure evaluation since it is relatively unaffected by changes in hole size, formation temperature, and formation water salinity.

The principle drawbacks of the above techniques have to do with the delay in obtaining such information relative to the potential immediate problems associated with abnormal pressures. For example, a sudden influx of formation fluids such as gas may indicate a potential blowout. Of the above techniques, those obtained "while drilling" are likely to be most helpful to prevent such a blowout from occurring. Such "while drilling" techniques would include drilling parameters, drilling mud parameters, and shale cutting parameters. The drilling parameters such as rate, drag, torque, etc., while occurring in "real time", are not sufficiently definitive to accurately predict the occurrence of a gas kick, for example. Drilling mud and shale cutting parameters are detected at the surface from the circulating mud stream and are delayed with respect to their real time occurrence by the time required for mud return from the bottom of the well bore.

Other detection techniques such as well logging and pressure measuring devices mentioned above are performed after drilling or during the cessation of the drilling operation. With the advent of deeper drilling and increased drilling activity offshore and in hostile surface environments, the costs of drilling have escalated substantially. Therefore, any operation which requires the cessation of drilling in order to be performed, such as lowering a wireline into the borehole, is done at great expense. With the current trend toward many wells being drilled to great depths, formation pressures as related to blowout potential is an increasing factor to be considered. Therefore, a greatly expanded need has arisen to obtain real time data relating to formation and drilling parameters. As a result much effort recently has been expended toward the development of telemetry systems to facilitate the use of measuring while drilling "MWD" techniques. Some of these telemetry systems are now becoming commercially available and as a result the need has arisen to develop downhole detection systems to obtain drilling and formation data to solve the problems enumerated above. The detection of abnormal formation pressures on a real time basis is a priority development in this respect. A basic indicator of abnormal formation pressure is the influx of hydrocarbon fluids or water into the borehole.

It is therefore an object of the present invention to provide a new and improved, simple, reliable and rugged method and apparatus for detecting, downhole, the influx of formation fluids into a borehole during a drilling operation.

SUMMARY OF THE INVENTION

With this and other objects in view, the present invention contemplates a borehole influx detector incorporated in a housing arranged for coupling a drill string. The detector measures parameters of the density of the borehole fluid which are compared with the nominal or average density of the drilling fluid to determine if formation fluids have flowed into the drilling fluid system.

In one embodiment of the invention, a radiation source and detector are mounted in a recess on the outer wall of a subassembly housing, so that a portion of the stream of drilling fluids passes through the transmission path of the source and detector. The detector count is determinative of the borehole fluid density. When discrete measurements of borehole fluid density are compared to nominal or average values of the fluid density, changes are indicative of formation fluid influx.

Another embodiment of the invention uses a highly collimated radiation source and detector which substantially counts only radiation passing through borehole fluids in the annulus between the housing and borehole wall.

In still another embodiment of the invention, radiation source and detector assemblies are mounted on the inner and outer walls of the subassembly housing so that a comparison of drilling fluid densities may be made between fluids before they exit the bit and after they have mingled with formation fluids to give an even more distinct comparison between fluid densities at these points in the drilling fluid system.

Another aspect of the invention involves the mounting of the radiation source and detector in a collimated in line configuration to provide a direct transmission path of radiation through the mud stream.

Yet another aspect of the invention involves the use of a relatively low strength radiation source for measuring drilling fluid density.

BRIEF DESCRIPTION OF THE DRAWINGS

FIG. 1 is a schematic elevational drawing of a drill string in a borehole and including an influx detector subassembly for carrying out the present invention;

FIG. 2 shows a schematic elevational view in cross section of a radiation source-detector assembly mounted in a subassembly housing for carrying out the present invention;

FIG. 7 shows a schematic elevational view in cross section of a subassembly housing for carrying out the present invention having radiation source-detector assemblies mounted both on the outer wall and on the inner wall.

DESCRIPTION OF PREFERRED EMBODIMENTS

Figure 3:
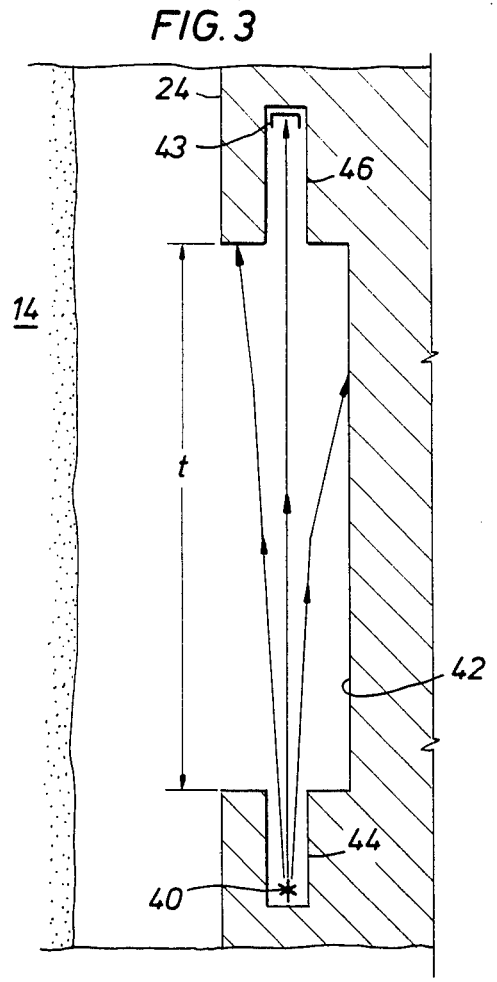
FIG. 3 shows a schematic elevational view of a direct transmission source-detector arrangement.

Referring first to FIG. 1 of the drawings, a borehole 12 is shown extending from the earth's surface 13 and penetrating earth formations 14. The borehole is being made by a drill string 16 principally comprised of a drill bit 18, drill collars or intermediate drill pipe 20 and sections of drill pipe 22 extending to the surface. A subassembly housing 24 is shown positioned above the bit 18 and serves to house an influx detector in accordance with the present invention. A telemetry subassembly 26 is shown positioned above the influx detector 24, and is used for telemetering data to the surface which is indicative of drilling fluid parameters measured downhole. At the surface 13, a surface telemetry receiver 28 provides a means for outputting data telemetered up the pipe string for passage of such data to a data processing unit 32. Here the data indicative of drilling fluid parameters is processed to provide an indication of the occurrence of downhole events such as formation fluid influx. Signals are developed in the data processing unit 32 indicative of such downhole events for passage to a readout device 34 for providing a detectable indication of the downhole event, such as an alarm or the like 34, as for example would be appropriate in the case of detection of a gas kick.

One downhole parameter which is indicative of the entry of formation fluids into the borehole is the density of drilling fluids. A system for determining drilling fluid density at a downhole location consists of a gamma ray detector which is arranged with appropriate electrical circuitry to measure changes in drilling fluid density and thereby detect the influx of formation fluids, especially gas, into the borehole. In this system, mud density is determined by measuring the passage of gamma rays through the mud from a source to a detector. Variations in mud density will cause the number of detected gamma rays to vary. Such a device will be described hereinafter with respect to FIG. 2 of the drawings. The detection devices described herein facilitate the use of a small, yet efficient gamma ray detector that can operate at the elevated temperatures of a borehole and which will be sufficiently rugged to operate on a drill string in a "while drilling" mode.

Mud density, or "mud weight", can vary during drilling for a number of reasons including variations in the quantity and density of cuttings entrained in the mud, changes in the "mud program" at the surface, temperature changes, etc. Mud density will also change when gas or liquid enters the borehole from the formation. By relating and correlating the measured changes in mud density with expected response due to cuttings, temperature, and the mud program, the detection of influx can be predicted. Influx will tend to cause a decrease in mud weight due to the entrainment of lighter formation fluids in the mud stream.

When gamma rays are passed through matter, they interact with the atomic electrons of the material. They are thereby attenuated by both atomic absorption (photo-electric effect) and scattering by the electrons. Mud weight fluctuations, i.e., variations in density ($\rho$), lead directly to variations in the electron density and thus to variations in the number of scattered and absorbed gamma rays passing through the mud. There are basically three modes available for observing or detecting variations in the number of gamma rays passing through the mud. These are as follows:

1. Detecting and counting those gamma rays that are directly transmitted from a source to a detector through mud unscattered;
2. Detecting and counting gamma rays which are scattered by the mud; and
3. Detecting and counting gamma rays both scattered by and transmitted through the mud.

The transmission approach which is shown schematically with respect to FIG. 3 includes directing a beam of gamma rays from a source 40 into a recess 42 in the outer wall of the subassembly housing, through which mud is flowing. A gamma ray detector 43 is axially aligned with the source 40 and both the source and detector are tightly collimated by collimating passages 44 and 46 which are constructed of a dense material, such as tungsten, to insure that a minimum of scattered gamma rays are observed. A good approximation of the number N of gamma rays that pass through the mud to the detector as shown in FIG. 3 is $$N = N_o e^{-\mu \rho t} \qquad (1)$$

where $N_o$ is the number of gamma rays that enter the mud in the direction of the detector, $\rho$ is the density of the mud, $\mu$ is the mass attenuation coefficient for mud, and t is the gamma-ray path length in the mud. For a typical mud $\mu$ is approximately 0.1 cm²/g, and $\rho$ is 1.5 g/cm³. The variation in counting rate at the detector due to variations in mud density will then be $$(\Delta N/N) = -\mu \rho t (\Delta \rho / \rho)$$

The factor relating fractional change in observed count and density, $-\mu \rho t$ in this case, is the sensitivity. For 10 cm mud thickness, $$(\Delta N/N) = -1.5(\Delta \rho / \rho)$$

that is, a one percent decrease in mud density will cause a one and one-half percent increase in counting rate. It is thus observed from these relationships that the sensitivity is maximized by choosing the largest practical value of the product $\mu \rho t$. This requires careful selection of $\mu$ and t to the range of mud densities expected to be encountered in drilling. The values of both $\mu$ and t depend on the source strength and type employed which, for ease of handling, the strength should be as small as possible. The lower limit on source strength is governed by the count rate required for acceptable statistics. Using a Geiger-Mueller tube (G-M tube) as a detector, the count rate is limited to some number of counts per second. This imposes a limit on the source strength and sensitivity. The reason for this is that the G-M tube becomes paralyzed for a short period when a count is detected. This means that if the detector is counting as fast as possible and, in the case of the present tool, an increase in density of the mud were to occur, a change in count rate will not be observed. Thus the upper limit in count rate is determinative of sensitivity. Also, as the detector approaches its paralyzed condition, its sensitivity is attenuated. A solid state detector is much less paralyzable and therefore the source strength is not limited in practice when using a solid state detector, except by source handling difficulties.

Figure 4:
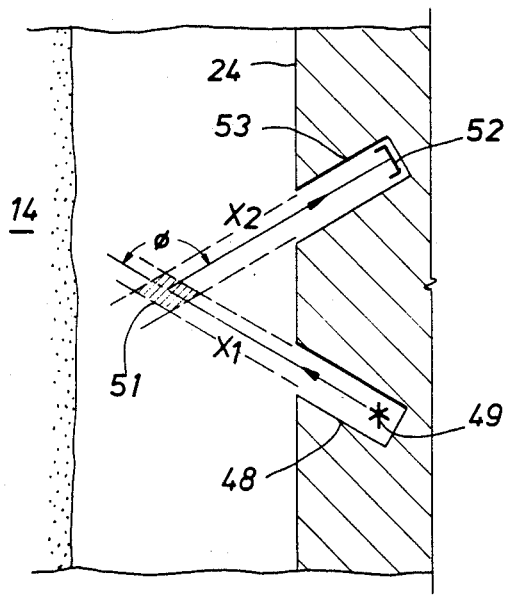
FIG. 4 shows a schematic elevational view of a single-scattered source-detector arrangement.
Figure 5:
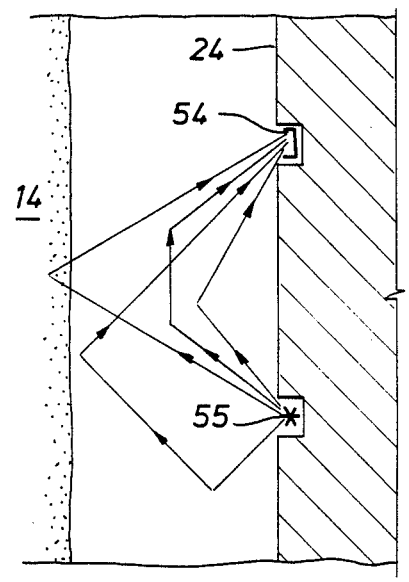
FIG. 5 shows a schematic elevational view of a diffusion source-detector arrangement.

The scattering approach, which is listed above as an alternative configuration of gamma-ray detection, is shown schematically in FIGS. 4 and 5. In this approach, the detector is shielded from direct radiation from the source. Of course there are innumerable variations to this concept of density measuring; however, the two extreme cases are depicted as the single scattering method in FIG. 4 and diffusion method in FIG. 5. The single scattering method of FIG. 4 used a tight collimating tube 48 to direct source 49 radiation toward inspection region 51. The detector 52 is likewise tightly collimated by passage 53 to receive only those rays scattered once from the inspection region or target 51. It is possible for multiple scattered radiation to be counted, but single scattering predominates. Because only a limited region is investigated, this approach, for that particular reason, is suited to drilling mud measurements. This assumes that collimation angles are choosen correctly and that the tool housing 24 is spaced sufficiently from the borehole wall of formation 14, to bring path lengths $x_1 + x_2$ into interception in the inspection region. Sensitivity is optimized by maximizing the quantity $1 - \rho (\mu_1 x_1 + \mu_2 x_2)$.

The terms of the above expression have opposite signs. Physically this occurs because an increase in mud density decreases the number of gamma rays that are transmitted along the paths $x_1$ and $x_2$; but increases the number that scatter from the inspection region. These two effects result in reduced sensitivity, which offsets the advantages of this method in the drilling environment. For practical collimator configurations, the sensitivity will range from about $-0.5$ to $+0.5$. Therefore, the single scattering approach will not be as sensitive as the transmission approach. Another drawback of the single-scattering concept is that very few gamma rays actually scatter into the detector. This implies the need for a relatively large source compared to the transmission approach for the same density resolution.

Figure 6:
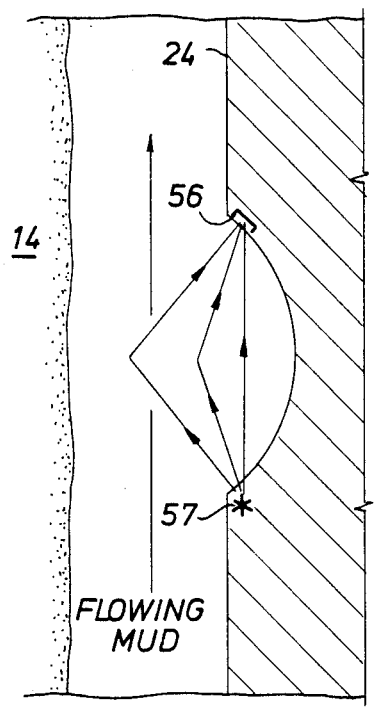
FIG. 6 shows a schematic elevational view of a combination of the source-detection techniques.

The diffusion approach for mud density gauging uses no collimation, as shown in FIG. 5. The detector 54 is shielded from direct radiation by the source 55, but is exposed to multiply scattered radiation over a large solid angle. The advantage of this method is simplicity of design and fabrication, and a higher counting rate than for single scattering geometry. There are two main disadvantages, i.e., (1) a relatively strong source 55 is needed to get a useful count rate; (2) the method is sensitive to the formation 14, which is undesirable. The sensor's response to gamma rays scattered from the formation can be reduced by decreasing the source-detector spacing. The approach shown in FIG. 6 is a configuration which allows the detector 56 to see both transmitted and scattered gamma rays from the source 57. The design is realized by using little or no colimation of either detector or source. The major advantage of this approach is the relatively high counting rate for a given source strength compared to the other methods. The sensitivity of the method will lie between the other two approaches.

In summary, the transmission method provides maximum sensitivity and a good counting rate. Scattering is least sensitive and has the lowest relative counting rate of the three methods. The combination of transmission and scattering gives the highest relative counting rate.

The requirements for a radiation source in the mud density measuring devices discussed above are satisfied by using 192 Ir, 137 Cs or 60 Co sources. The basic requirements of a source in this application are (1) the gamma rays must be able to penetrate at least several inches of mud, but the attenuation of the gamma radiation should be large enough to maximize the sensitivity; (2) that the source strength must be sufficient to provide adequate counting statistics, but no larger; and (3) the sources' active life-time must be at least a sizeable fraction of a year.

In the source-detector configurations described above, a source strength of 0.1 of a Curie would be sufficient to operate in the direct transmission technique and a source of one Curie would suffice for the other approaches.

The radiation detector must operate effectively at borehole temperatures, should have relatively high counting efficiency, must be physically small, and must be rugged. The G-M counter fulfills these requirements. The influx sensors described above, using density monitoring techniques, are capable of resolving 1% increments in fluid density.

Referring next to FIG. 2 of the drawings, an influx sensor of the direct transmission type is shown in greater detail. The subassembly housing 24 is made from a thickwall section of pipe such as a drill collar, having a longitudinal bore 62 extending through the sub 24. Threaded connecting surfaces (not shown) are provided at each end of the sub to facilitate assembly into a drill string. The outer wall surface of the housing 24 is provided with a recessed flat 64 machined on the outer surface of the housing. The flat is recessed a sufficient depth into the housing wall to accommodate a mud density detector, yet leaves a sufficient wall thickness in the housing adjacent the recessed flat to maintain the structural integrity of the subassembly when utilized in a drill string.

A source-detector assembly is shown mounted in the recessed flat 64 and comprises a sensor-source insert 66 which has an inward facing flat surface for matingly engaging the flat 64. The insert 66 has a hollow chamber 67 formed within the insert at its upper end and a longitudinal cylindrical detector cavity or chamber 68 extending downwardly from the chamber 67. A detector collimating passage 69 extends longitudinally downwardly from the detector cavity 68, such passage 69 intersecting with a longitudinal recessed groove 71 formed along the outer face of the insert 66. The groove has radii 72 and 73 formed at its upper and lower ends respectively, such radii serving to provide a streamlined surface between the outer wall of housing 24 and the recessed groove 71 on the outer face of insert 66. The lower end of insert 66 has a recessed chamber for receiving a source mount assembly 76. The source mount assembly 76 includes a source mount 77 onto which is mounted a radiation source 78. A source collimating passage 79 extends from the upper end of the source chamber to intersect with the radius 73 on the recessed groove 71 of insert 66. The radiation source 78 is arranged to be housed within the lower end of passage 79. Windows 81 are mounted within window recesses on the radii 72 and 73 and serve to cover the outer ends of collimating passages 69 and 79 respectively. The windows are constructed of a material having a low electron density or low atomic number such as titanium. Such a window provides an impervious seal to wellbore fluids and permits substantially unattenuated passage of radiation through the passages 69 and 79.

At the lower end of insert 66, a source mount plug 84 is shown positioned within a recess on the lower end of insert 66. O-ring seals 87 are positioned in grooves on the outer surface of plug 84 to seal the lower end of the source chamber from well fluids. A transverse opening 88 extends through the plug 84 for receiving a holddown screw 89 which is threadedly received in the outer wall of the recess 64 on housing 24. Clamp plate 91 is likewise held by screw 92 onto housing 24. Clamp plate 91 and plug 84 have mating shoulder portions 93 and 94 respectively to facilitate clamping the lower end of insert 66 into the recess 64.

At the upper end of insert 66, an upper plug 96 is shown having a cap portion 97 with O-ring seals 98 for sealing off the upper end of chamber 67. Chamber 67 is provided for housing circuit components associated with a Geiger-Mueller detector 99 arranged within the chamber 67 and detector chamber 68. The upper plug 96 is arranged to receive a screw 101 for threadedly securing the upper end of insert 66 against the recessed surface 64 of the housing 24. Connecting passages 102 in the plug are arranged to provide a means for extending conductor wires from an electrical connector in plug 96 to associated electronics 104 mounted in housing 24 above the density detector heretofore described.

While the apparatus described above has for the most part been referenced to a gamma ray detector for measuring mud density to determine influx, it is readily seen that other instruments as well as other types of radiation detectors could be used to provide such density measurements. Additionally, while the gamma ray detector shown in FIG. 2 is primarily in a direct transmission configuration, it is seen that other arrangements, such as the highly collimated single scattering technique of FIG. 4, also provide a workable solution of this problem.

In the operation of the apparatus described above, the detector housing 24 is run into the wellbore on the drill string 16 and is arranged to operate during the entire drilling operation, including the tripping of the drill string. A suitable telemetry system including a downhole telemetry package 26 and surface receiver 28 is used to transmit data signals developed in the detector subassembly 24. The detector primarily described herein is comprised of a suitable radiation source 78 and a suitable detector such as G-M detector 99. As drilling fluids in the downhole annulus pass the recessed surface 71 on the source-detector insert 66, gamma rays emitting from source 99 are transmitted or scattered (depending on detector configuration) through the drilling fluid whereupon a portion of such gamma rays are received within the detector collimator for passage to the detector which counts the gamma rays received. If an influx of formation fluids into the annulus occurs, the density of the drilling fluids will be decreased sufficiently at that position in the annulus to be detected readily by the gamma ray detector. The gamma ray detector transmits its counts into storage either in downhole electronics or by telemetry to the surface. These counts are then averaged as by the data processor 32. When a count appears that is significantly different than the average or nominal count in storage, the system is alerted that a potential influx is occurring. If the abnormal count persists, say for another period and is significantly different in magnitude from the nominal count, a surface signal such as alarm 34 may be activated to forewarn the possibility of a blowout. Alternatively, rather than comparing with nominal or average counts, the processor can plot a log versus time or depth as data is collected to watch for trends.

FIG. 7 illustrates an alternative arrangement provided by also mounting a density detector as shown in FIG. 2 on the inner wall of the housing 24, and displaced longitudinally slightly from the outer wall detector for structural integrity of the unit. The components of this inner detector correspond to the previously discussed and identified components of the outer detector illustrated in FIG. 2. The components of the inner detector have been identified by reference numbers obtained by adding 100 to the reference numbers of the corresponding components of the outer detector illustrated in FIG. 2. The detector on the inner wall of the housing would be counting the density of fluid returning from the mud pits to the bit, thus distanced by substantial circulating time from influx formation fluids. The outer wall detector would take counts of the borehole fluid including any influx fluids occurring at that time. A comparison of these density determinations would give a more precise evaluation of what was occurring at that discrete position in the borehole where the outer detector was operating.

Other techniques, such as downhole recording, with or without telemetry, can also be utilized for processing the data within the scope of the present invention.

The foregoing disclosure and description of the invention is illustrative and explanatory thereof, and various changes in the method steps as well as in the details of the illustrated apparatus may be made within the scope of the appended claims without departing from the spirit of the invention.

We claim:

1. An apparatus for detecting the influx of formation fluids into a borehole and capable of being used in a drill string during a drilling operation, comprising:
    a housing capable of being coupled in a drill string;
    a radiation source means mounted on said housing;
    a radiation detection means spaced from said radiation source means on said housing, said detection means for detecting radiation from said source means which has substantially only passed through the fluids in said borehole.

2. The apparatus of claim 1 further comprising recess means formed in the wall of said housing, said recess means being in the flow path of the fluids passing along a wall of said housing, the wall thickness of said housing adjacent said recess means being sufficient to maintain the structural integrity of said drill string.

3. The apparatus of claim 2 further comprising means for collimating the source radiation through said recess means to said detector means.

4. The apparatus of claim 3 wherein said collimating means comprises longitudinal chamber means at opposite ends of said recess means for housing said radiation source means and said radiation detection means respectively.

5. The apparatus of claim 3 wherein said collimating means comprises longitudinal collimating passages arranged in said recess means so that said passage associated with said radiation source means is axially aligned with said passage associated with said detecting means.

6. The apparatus of claim 5 wherein said collimating passages are closed at their outer ends by a thin window of material having a low electron density.

7. The apparatus of claim 1 wherein said detecting means includes a plurality of detectors mounted in the wall of said housing.

8. The apparatus of claim 1 further comprising a central passageway axially through said housing for permitting the passage of drilling fluids therethrough.

9. The apparatus of claim 8 wherein said radiation detection means includes detectors mounted on the interior and exterior wall surfaces of said housing.

10. The apparatus of claim 9 further comprising means for comparing the detected radiation of the exterior detection means and the interior detection means for determining the relative densities of the fluid in said central passageway and the fluid exterior of said housing.

11. A borehole logging apparatus mounted in a drill string for use in a drilling operation, including:
    a housing arranged for coupling in a string of pipe and having a central passageway therein for permitting the passage of a drilling fluid therethrough;
    recess means on the external wall of said housing in the flow path of drilling fluids passing along said housing;
    the wall thickness of said housing transversely adjacent said recess means being sufficient to maintain the structural integrity of said housing in said drill string; and
    means mounted in said recess means for detecting the density of drilling fluids passing along said housing by detecting radiation which has substantially only passed through said drilling fluids from a radiation source on said housing.

12. The apparatus of claim 11 and further including means on the internal wall of said housing for detecting the density of drilling fluids passing through said central passageway of said housing.

13. The apparatus of claim 11 wherein said radiation source and detector are arranged so that said detector substantially detects only radiation passing through drilling fluids.

14. A method for determining density of a drilling fluid during a drilling operation including the steps of:
    positioning an annular housing in a drill string which housing includes a density measuring device comprising a radiation source and a radiation detector spaced therefrom;
    running the density measuring device into the borehole on the drill string;
    measuring the density of the drilling fluids in the drilling annulus at a downhole location by detecting with said radiation detector radiation from said radiation source which has substantially only passed through said drilling fluids; and
    telemetering data to the surface indicative of the density of downhole fluids.

15. The method of claim 14 and further including comparing the average density of downhole fluids with discrete density measurements of downhole fluids to determine the influx of formation fluids into the borehole.

16. The method of claim 14 wherein such drilling operation employs the use of drilling fluids passing downwardly through the drill string including the housing and returning to the surface through the drilling annulus and further including: measuring the density of drilling fluids passing through the drill string, and comparing the density of the drilling fluids with the density of fluid in the drilling annulus.

17. The method of claim 14 wherein said radiation source and detector are axially aligned on said housing and further including detecting substantially only radiation transmitted unscattered through the downhole fluid.

18. A method for detecting during drilling, the influx of formation fluids into a borehole being drilled by a drill bit operating on a drill string and utilizing a drilling fluid passing through the drill string and up the borehole annulus to the surface, including the steps of:

positioning at least one radiation source and detector in a housing and incorporating such housing in a drill string;

running the housing into the borehole on the drill string;

counting that radiation which passes from the source to the detector through the borehole fluids when such source and detector are immersed in borehole fluids; and detecting changes in the radiation count to determine the influx of formation fluids into the borehole.

19. The method of claim 18 and further including telemetering data to the surface indicative of detected radiation counts.

20. The method of claim 18 wherein said radiation source and radiation detector are axially aligned in the direction of the longitudinal axis of said drill string and further including counting substantially only radiation which passes unscattered through such borehole fluids between the source and detector.

21. The method of claim 18 and further including collimating the radiation path between the source and detector to attenuate the detection of radiation which has scattered from the source into material other than the borehole fluid.

22. Apparatus for measuring changes in the density of a drilling fluid during a drilling operation, including:

housing means arranged for mounting in a drill string;

means mounted on said housing for detecting discrete values of density of drilling fluids passing said housing at a downhole location comprising radiation source means on said housing means and radiation detection means spaced therefrom on said housing means for detecting radiation substantially passing only through said drilling fluids;

means on said drill string for telemetering data signals to the surface; and means for providing data signals to said telemetering means indicative of the density of such drilling fluids.

23. The apparatus of claim 22 and further including means for comparing nominal density of the drilling fluids with discrete measured values of drilling fluid density.

24. The apparatus of claim 22 wherein said radiation source has a radiation strength of less than one tenth of a curie.

25. The apparatus of claim 22 wherein said density detecting means is comprised of a radiation source and detector, with said source having a radiation strength of less than one curie.

26. Apparatus for measuring the density of drilling fluids in a borehole during a drilling operation, including:

a housing arranged for coupling in a string of pipe having a central passageway therein for passage of a drilling fluid therethrough;

radiation source means mounted on the outer wall of said housing;

radiation detector means mounted in the outer wall of said housing; and collimating means associated with said radiation source means and detector means for substantially directing the path of radiation between said source means and detector means only through borehole fluids.

27. The apparatus of claim 26 wherein said source means and detector means are positioned within a recess in the outer wall of said housing and are axially aligned to permit substantially only the direct transmission of radiation between said source means and detector means.

28. The apparatus of claim 26 wherein said source means and detector means are angularly collimated with respect to the longitudinal axis of said housing to a precise extent such that substantially only radiation scattered from the annular space between said housing and the borehole wall containing borehole fluids is received by said detector means.

29. The apparatus of claim 26 and further including second radiation source and detector means mounted on the inner wall of said passage in said housing.

30. The apparatus of claim 29 wherein said second radiation source and detector means are spaced longitudinally in the housing from the radiation source and detector means on the outer wall of said housing to provide structural integrity to said housing.

31. The apparatus of claim 29 and further including means for counting the radiation received from said detector on the outer wall of said housing and the radiation received by said second detector on the wall of said passage in said housing; and means for comparing the counts received by the respective detectors.

* * * * *